(12) United States Patent
Darst et al.

(10) Patent No.: US 7,200,906 B2
(45) Date of Patent: Apr. 10, 2007

(54) EARTH CONTACT BURIAL CONTAINER, BURIAL SYSTEMS AND METHODS

(75) Inventors: Joseph P. Darst, 4326 Columbia, Pasadena, TX (US) 77504; Thomas C. Knickerbocker, 2305 Dauphin Ct., Nassau Bay, TX (US) 77058; Julie A Fenimore, McKinney, TX (US); Ralph P. Moresco, 3796 Ranch Road 261, Buchanan Dam, TX (US) 78609

(73) Assignees: Thomas C. Knickerbocker, Nassau Bay, TX (US); Joseph P. Darst, Pasadena, TX (US); Ralph P. Moresco, Buchanan Dam, TX (US)

( * ) Notice: Subject to any disclaimer, the term of this patent is extended or adjusted under 35 U.S.C. 154(b) by 123 days.

(21) Appl. No.: 10/811,183

(22) Filed: Mar. 26, 2004

(65) Prior Publication Data
US 2005/0210642 A1 Sep. 29, 2005

(51) Int. Cl.
*A61F 17/00* (2006.01)
(52) U.S. Cl. .............................................. 27/2; 52/128
(58) Field of Classification Search ...................... 27/2, 27/35; 52/128–131, 139
See application file for complete search history.

(56) References Cited

U.S. PATENT DOCUMENTS 2,356,957 A * 8/1944 Turner ............................ 27/35
2,927,453 A * 3/1960 Patterson et al. .............. 52/133
3,230,674 A * 1/1966 Christensen ................ 52/127.1
3,273,294 A * 9/1966 Trzesniewski ................ 52/141
3,439,461 A * 4/1969 Chandler et al. .............. 52/139
4,099,353 A 7/1978 Blunt
4,200,944 A * 5/1980 Gillespie et al. ............ 114/343
4,476,657 A 10/1984 Juba et al.
6,453,626 B1 9/2002 Weilein et al.

* cited by examiner

*Primary Examiner*—William L. Miller
(74) *Attorney, Agent, or Firm*—Howison & Arnott, L.L.P.

(57) ABSTRACT

A burial container having an enclosure for a body and an opening in the bottom to permit earth to be communicated into the container and allow the body within to be in contact with the earth. At the same time, the body is enclosed, in accordance with a number of existing laws regarding burial. In preferred embodiments, a mound of earth is placed within the container having a slope that causes the body to reside on its side, so that it may face Mecca. A burial field is placed atop the ground surface rather than below it and with an engineered drainage field beneath the containers groundwater is not affected. The resulting graves are then above the previous natural ground and the entire field will have the appearance of a mound. A burial field may be established that contains a plurality of burial containers that are oriented such that, upon burial, bodies will face toward Mecca.

18 Claims, 5 Drawing Sheets

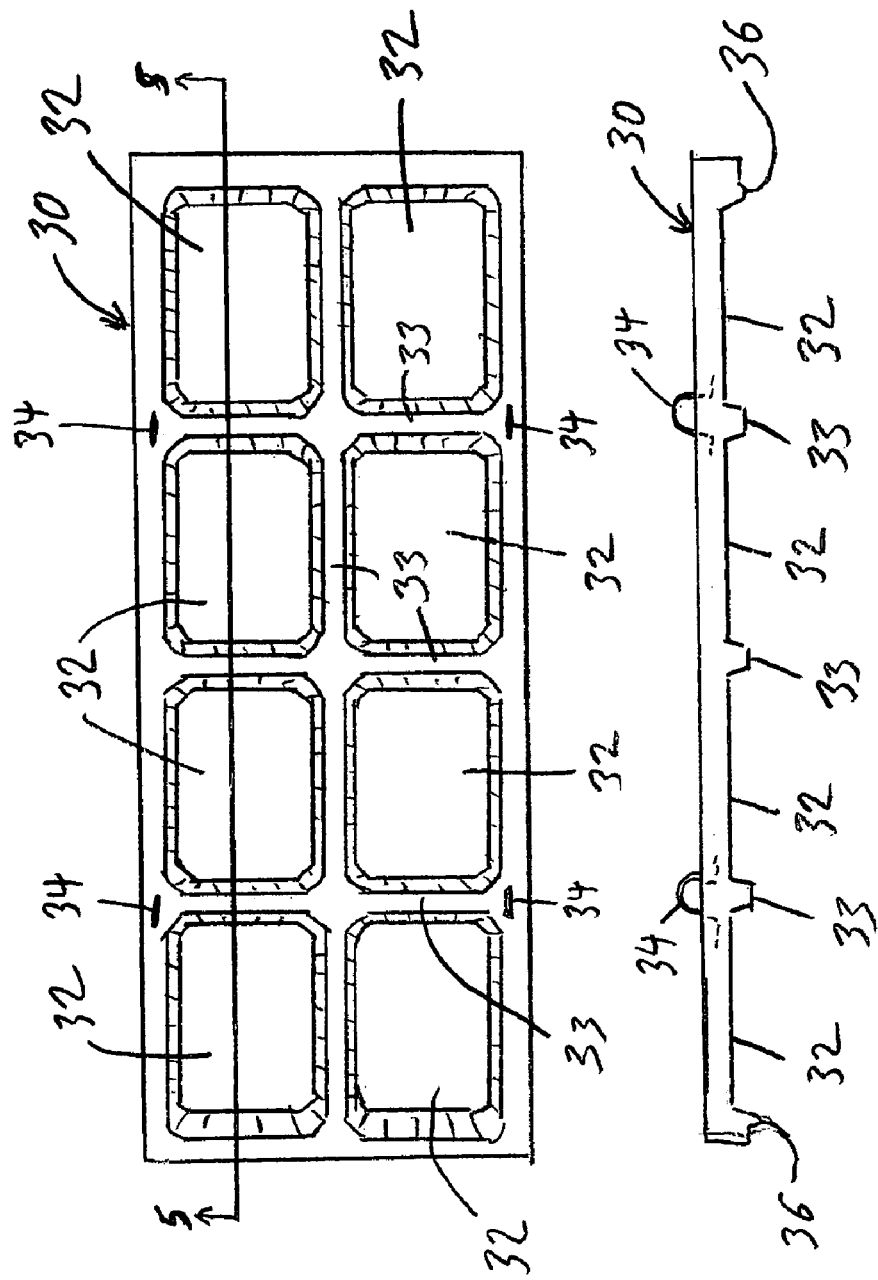

Burial Field with graves oriented to Mecca (K'abba)

EARTH CONTACT BURIAL CONTAINER, BURIAL SYSTEMS AND METHODS

BACKGROUND OF THE INVENTION

1. Field of the Invention

The invention relates generally to burial containers. In certain aspects, the invention also relates to burial systems and methods of burial.

2. Description of the Related Art

The Islamic faith requires the dead to be buried without being encased in a casket, with the body in full contact with the soil, and lying on its left side facing Mecca. The true compass line from the body must align precisely with Mecca. Currently, the alignment is determined by surveying methods and then certified by clerics of the Islamic Faith before the burial field will be consecrated for use. The Jewish faith also has classes of believers who believe that the body should be buried in full contact with the earth below, although the orientation of the grave is not required to be in a particular alignment.

Conventional caskets, crypts and other burial containers are problematic since they separate the body from the earth. Examples of such burial containers are found in, for example, U.S. Pat. No. 6,453,626 issued to Weilin et al; U.S. Pat. No. 4,476,657 issued to Juba et al.; and U.S. Pat. No. 4,099,353 issued to Blunt.

While it is possible to bury human remains directly without a casket or container such is not possible within the cemetery laws extending to perpetual care cemeteries in the United States and some foreign countries. Existing operators have provided burial of members of the Islamic and Jewish faiths but as yet have not done so providing full contact with the ground and doing so with the burial field established and consecrated before need. Existing operators have not established and constructed large burial fields by placing a number of containers in the ground and then covering them, landscaping and marking them in advance of need. Existing operators tend to excavate burial plots either singly or in number and then backfilling to return the land to its former elevation. This creates a problem in that drainage cannot be directed away from the burial container and the result is containers will fill with water and contamination can occur as decomposition advances.

The present invention is directed to overcoming the problems of the prior art.

SUMMARY OF THE INVENTION

The present invention provides a burial container that provides an enclosure for a body and an opening in the bottom to permit earth to be communicated into the container and allow the body within to be in contact with the earth. At the same time, the body is enclosed, in accordance with a number of existing religious customs and regulations regarding burial. In preferred embodiments, a mound of earth is placed within the container having a slope that causes the body to reside on its side, so that it may face Mecca.

In preferred embodiments, a burial field is placed atop the ground surface rather than below it and with an engineered drainage field beneath the containers groundwater is not affected. The resulting graves are then above the previous natural ground and the entire field will have the appearance of a mound.

In other aspects, the invention provides methods and systems of burial wherein a burial field may be established that contains a plurality of burial containers that are oriented such that, upon burial, bodies will face toward Mecca.

BRIEF DESCRIPTION OF THE DRAWINGS

For detailed understanding of the invention, reference is made to the following detailed description of the preferred embodiments, taken in conjunction with the accompanying drawings in which reference characters designate like or similar elements throughout the several figures of the drawings.

FIG. 4 depicts an exemplary removable lid for the container shown in FIGS. 1–3.

FIG. 5 is a cross-sectional view of the lid taken along lines 5—5 in FIG. 4.

DETAILED DESCRIPTION OF THE PREFERRED EMBODIMENTS

Figure 1:
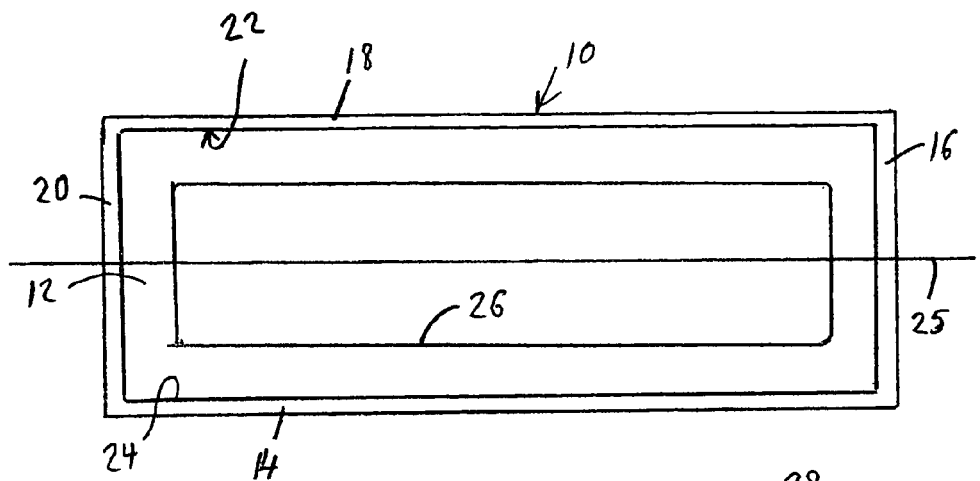
FIG. 1 is a plan view of an exemplary burial container constructed in accordance with the present invention.
Figure 2:
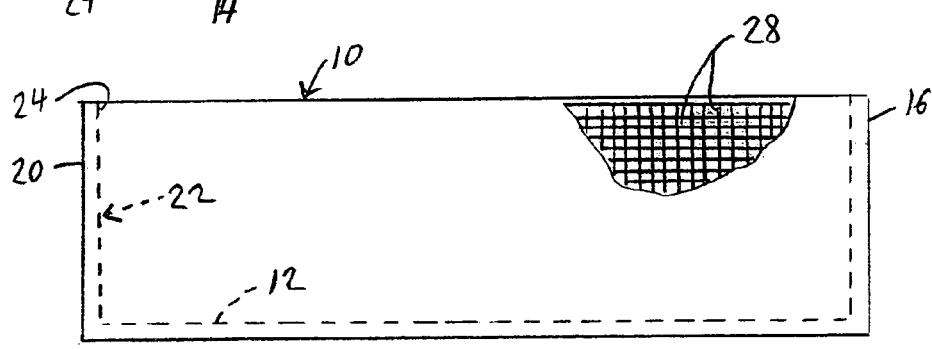
FIG. 2 is a side view of the container shown in FIG. 1.
Figure 3:
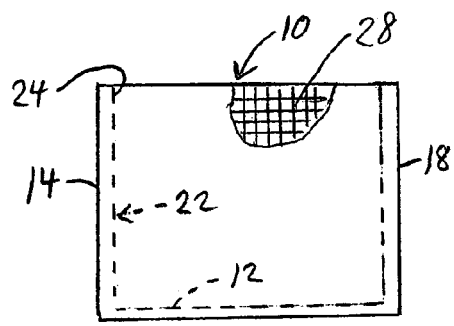
FIG. 3 is an end view of the container shown in FIGS. 1 and 2.

FIGS. 1–3 depict an exemplary burial container 10 in accordance with the present invention. The container 10 includes a bottom panel 12 and four side panels 14, 16, 18, 20 that define a container body with an interior enclosure 22. A top opening 24 is provided for placement of a body into the container 10. The container 10 has a longitudinal axis 25. An open section 26 is formed within the bottom panel 12. The burial container 10 is preferably fashioned of strong, reinforced concrete. It is currently preferred that the container 10 be manufactured with 3,000 psi Portland Cement concrete. The panels 12, 14, 16, 18, 20 of the container 10 are each cast with reinforcing steel 28, in a manner known in the art for providing tensile strength to the panel. A presently preferred reinforcement scheme is the use of #10 welded 2×2 wire mesh reinforcement steel. When the lower panel 12 is cast, the reinforcing steel 28 extends across the lower opening 26 and is then cut away after the panel 12 has cured. A currently preferred size for the burial container 10 is 90 inches in length, 34 inches in width, and 27 inches in height. The lower opening 26 is preferably 74 inches in length and 23 inches in width, leaving a surrounding supporting surface, or shelf, in the lower panel 12. The shelf provided by the panel 12 provides structural integrity and stability for the container 10 during handling and movement of the container 10. The panels 12, 14, 16, 18, 20 are preferably about 2 inches thick. It should be understood that these dimensions are not intended to be limiting, as those of skill in the art will understand that the burial container 10 may be made in any desired size, including, for example, smaller containers for the bodies of children.

FIGS. 4 and 5 depict a lid 30 for the container 10. The lid 30 is preferably formed of the same material as the container 10 and includes reinforcing steel just as the panels 12, 14, 16, 18, and 20 of the container 10 do. The lid 30 is preferably provided with a plurality of indentations 32 that reduce the thickness of the lid 30 in certain areas, thereby making the lid 30 lighter. Beams 33 are defined between the indentations 32 and serve to reinforce the lid 30.

Lifting eyes 34 are cast into the lid 30 and are preferably formed of stainless steel to reduce rust and corrosion potential. Additionally, the lid 30 includes a peripheral lip 36 that fits within the top opening 24 of the container 10. The lid 30 is cast to completely seal the container via lip 36 and its chamfered outer surface that centers the lid 30 in the open container 10. When emplaced, the lip 36 extends approximately one inch into the container 10.

Figure 6:
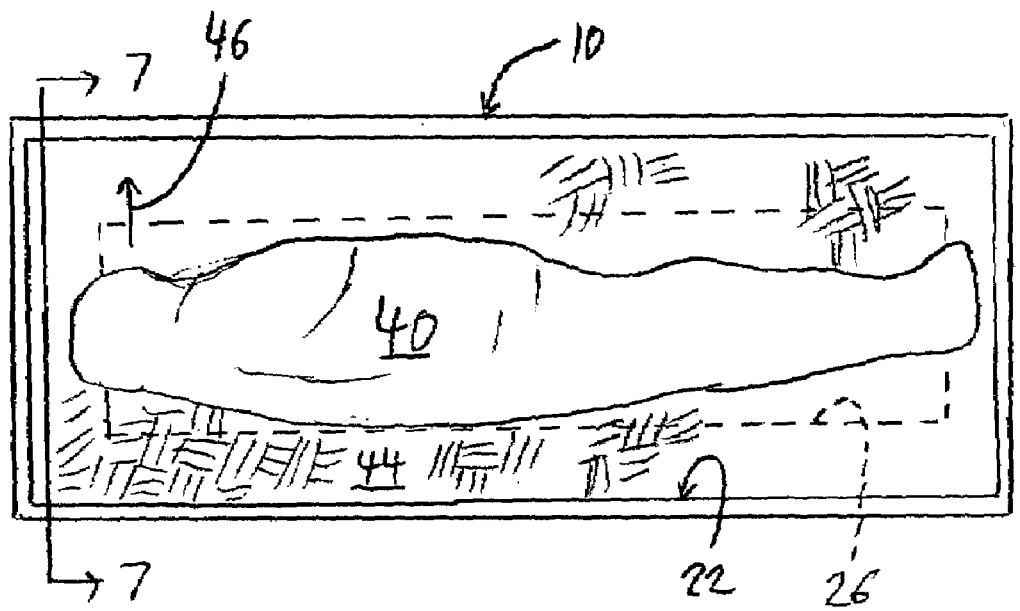
FIG. 6 is a plan view depicting a body inside of the burial container shown in FIGS. 1–3.
Figure 7:
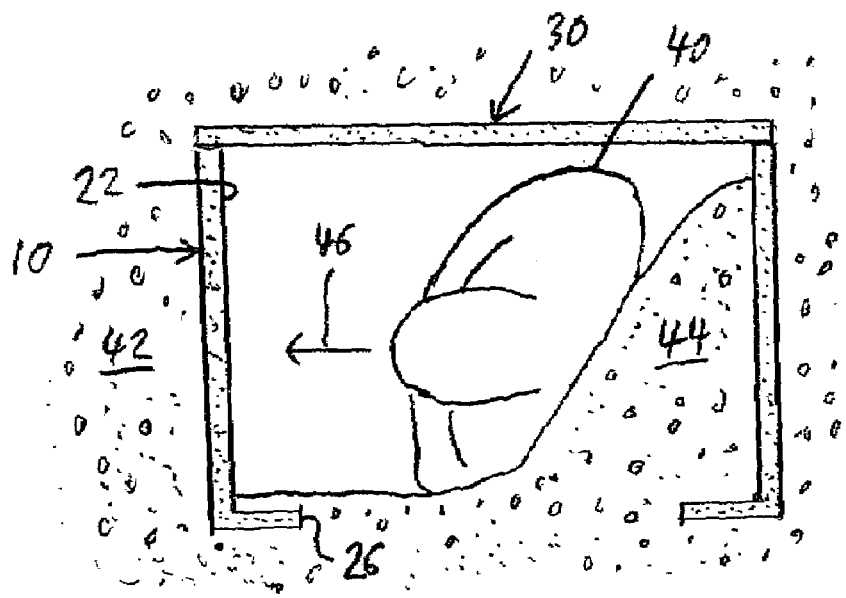
FIG. 7 is a cross-section taken along lines 7—7 in FIG. 6.

The lower opening 26 is an important feature of the present invention as it allows direct communication between the interior enclosure 22 defined by the container 10 and the earth beneath the container 10. FIGS. 6 and 7 illustrate a cloth-wrapped body 40 within the container 10 and covered by lid 30. The container 10 is buried within the earth 42. The body 40 lays atop a mound 44 of soil which is banked at an approximate 45 degree angle, thereby causing the body 40 to reside on its left side, as shown, and face in the direction indicated by arrow 46. As particularly evident from FIG. 7, the body 40 is in contact with the mound 44 which, by virtue of the lower opening 26 is in communication with the earth 42 below and surrounding the container 10.

Figure 8:
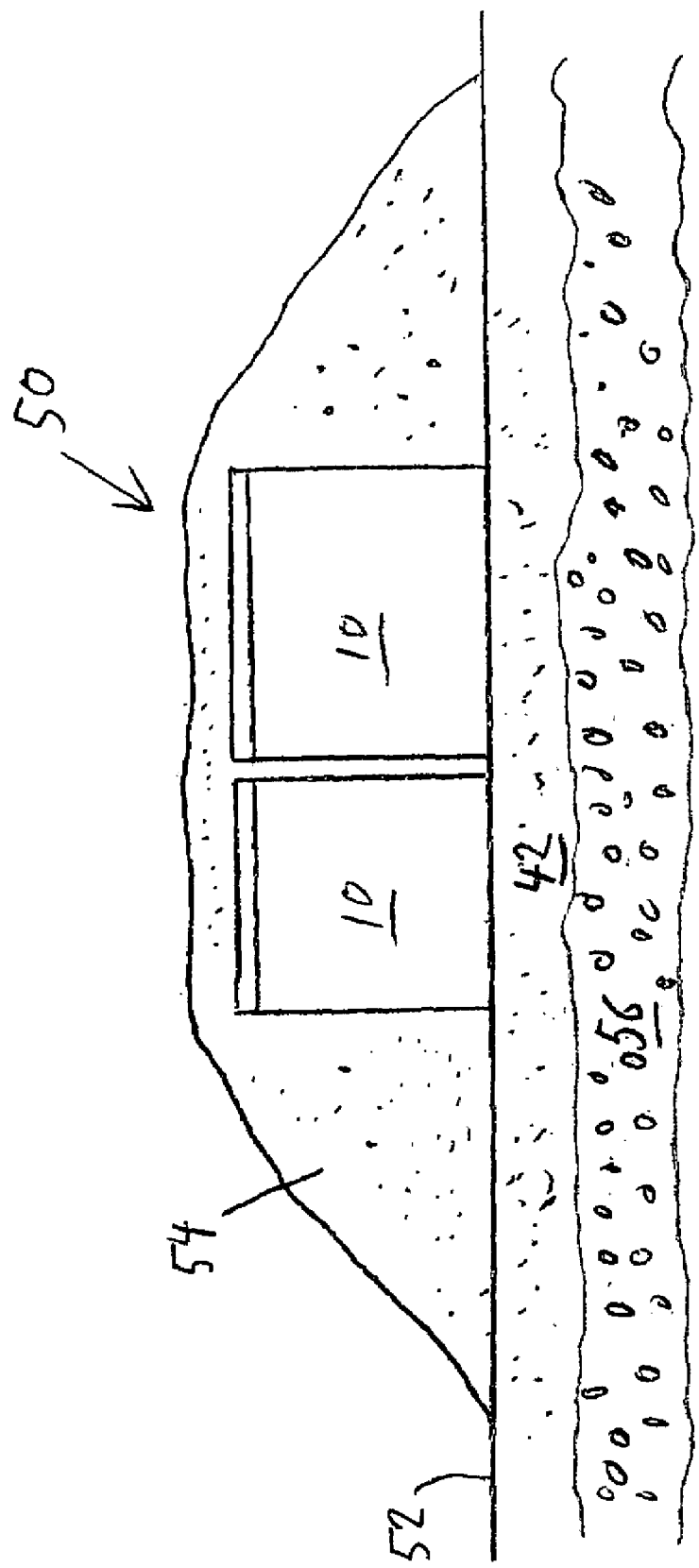
FIG. 8 is a perspective view of an exemplary burial mound in accordance with the present invention.

FIG. 8 depicts a typical burial mound 50 having two burial containers 10 therein. There may, of course, be more or fewer than two containers in a particular burial mound. The mound 50 is similar to the pre-historic mounds discovered throughout the country that were designed by Indian tribes. To construct the mound 50 he containers 10 are placed atop the ground 52 and then covered with earth 54. Preferably, a layer 56 of rock underlies the ground 52 to provide drainage.

Figure 9:
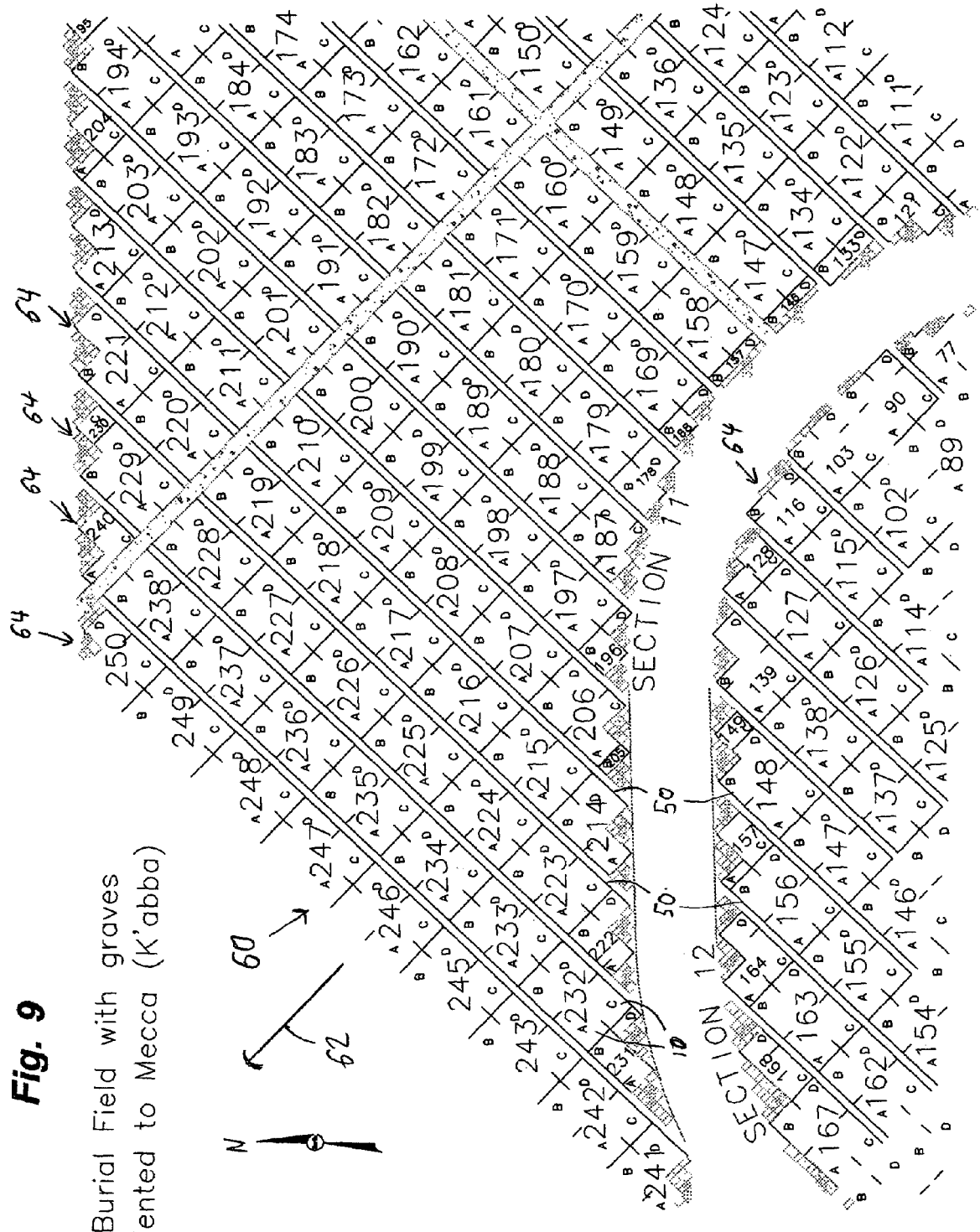
FIG. 9 is a plan view of a portion of an exemplary cemetery in accordance with the present invention.

FIG. 9 illustrates a burial field 60 within a cemetery, in accordance with the present invention. The burial field 60 is shown separated into two sections, section 11 and section 12. Burial mounds 50 are depicted schematically and are shown to include a number (typically four) individual containers 10 (designated A, B, C, and D in FIG. 9). The burial mounds 50 are oriented so that the longitudinal axis 25 of each container 10 lies normal to the direction of Mecca, shown as arrow 62. This ensures that, when a body is placed into the container 10 on its side, it will be facing Mecca.

A typical cemetery incorporating burial mounds 50 is first designed into phases or sections that are subscribed to by a Mosque, Synagogue or other membership faith organization. This reserves the entire section or phase for the perpetual use of the members. The field is than surveyed using Global Positioning (GPS) data collection equipment, of a type known in the art, and calculations are made to the true azimuth of the courtyard of the Great Mosque of Mecca (the Ka'aba). The current state of the art is limited to approximations of the true azimuth of Mecca but in fact the holy courtyard of the Mosque, named the Ka'aba, can be precisely oriented using modern global positioning systems and state plane coordinates or geographic coordinates. The surveyor establishes a true line of bearing 62 to the Ka'aba and this is shown to and accepted by a member of the Islam faith who has the authority to consecrate the graves 20 of believers. The line 62 is marked with monuments and perpendicular lines are then surveyed. These lines will become the columns 64 of the burial mounds 50. The burial field 60 is then stripped of surface vegetation and leveled to provide a base for the containers 10 to be placed. The base is then compacted to provide structural support for the containers and the layer 56 of rock is placed over then entire field 60. This is leveled again and then the containers 10 are placed on the column lines and verified as to the perpendicular orientation. Containers 10 are typically placed side by side except where surface pathways are to be constructed or where irrigation lines (not shown) are to be placed to water the finished grass area covering the entire field 60.

Once all containers 10 are in place, the stripped soil and additional soil as needed are spread over the entire field to a depth specified by law (typically from 4 to 10 feet deep). Sod or seed is installed over the field 60 and monuments for each grave block/burial mound 50 may be installed. These can be located at a corner of each block or in the center. Perimeter steel rods (not shown) are driven into the ground to allow positive identification of the corners of each block and burial plot. Numbers and or letters are assigned and final engineering drawings or plats are prepared and field verified. The plat is then recorded in public map or real estate records and, in the case in Texas, a certified copy is sent to the State Banking Commission. Another certified copy is given to the subscribing group who has purchased the rights to inter for the section or phase.

In another embodiment of the invention crypts are placed when actually needed in the customary orientation of the cemetery and these are used primarily by members of the Jewish faith who desire full ground contact by the body. The invention and pre-need preparation of a burial field is also possible in a large phase for subscription by groups in this faith and the process is the same with the exception that no orientation to Mecca is required. Layout of phases in this instance would be either defined by the cemetery owner or the faith group when it is being initially designed.

The burial technique is an adaptation of the Muslim procedure of placing the body on its side facing the Holy City of Mecca (in this case the precise orientation to the Ka'aba). Embodied in this invention is a process of installing a layer 44 of clean native soil into the container and creating a back stop that will keep the body on its side forever. Soil 44 is hand placed in a mound inside the container 10 sloping up the sidewall behind the body until it firmly holds the body. This creates a uniform layer of earth that also fills the lower opening 26 resulting in complete contact of the body 40 with the earth 42 below the container 10.

The systems and methods of the present invention allow burial of Islamic and Jewish believers (and others who may prefer such method of interment who are not necessarily of those faiths) in conformance with their teachings and faith and eliminates the necessity of private burial grounds that cannot meet the legal requirements for a perpetual care cemetery.

Those of skill in the art will recognize that numerous modifications and changes may be made to the exemplary designs and embodiments described herein and that the invention is limited only by the claims that follow and any equivalents thereof.

What is claimed is:

1. A burial container for burying a body comprising:
 a container body defining an enclosure and an upper opening through which the body is adapted to be placed into the enclosure; and
 a lower panel having an opening formed therein to permit communication of earth with the interior of the enclosure;
 the opening sized such that the body will be in direct contact with the earth when the body is placed in the enclosure and at the time of such placement, the opening comprising the majority of the surface area of the lower panel.

2. The burial container of claim 1 further comprising a removable lid for the upper opening.

3. The burial container of claim 2 wherein the lid is provided with a lifting eye.

4. The burial container of claim 3 wherein the lifting eye is formed of stainless steel.

5. The burial container of claim 1 wherein the container body is made of concrete.

6. The burial container of claim 5 wherein the container body includes reinforcing steel.

7. A burial container for burying a body comprising:
   a container body having four side panels that define an enclosure and a top opening through which the body is adapted to be placed into the enclosure;
   a lower panel affixed to the four side panels and having a central opening formed therein to permit communication of earth with the interior of the enclosure, such that the body will be in direct contact with the earth when the body is placed in the enclosure and at the time of such placement, the central opening comprising the majority of the surface area of the lower panel; and
   a removable lid for closing the top opening.

8. The burial container of claim 7 wherein the container body and lid are fashioned of steel reinforced concrete.

9. The burial container of claim 7 further comprising a plurality of rust-resistant lifting eyes secured to the lid to permit lifting of the lid from the container body.

10. The burial container of claim 7 further comprising a peripheral lip on the lid for engagement of the top opening when the lid is placed on the container body.

11. The burial container of claim 7 further comprising an indentation in the lid for reduction of weight.

12. The burial container of claim 7 wherein the lower panel defines a shelf surrounding the central opening.

13. A burial container for burying a body comprising:
    a container body having four side panels that define an enclosure and a top opening through which the body is adapted to be placed into the enclosure;
    a lower panel affixed to the four side panels and having an opening formed therein that is shaped and sized to permit direct communication between the body in the enclosure and earth beneath the container body, such that the body will be in direct contact with the earth when the body is placed in the enclosure and at the time of such placement, the opening comprising the majority of the surface area of the lower panel.

14. The burial container of claim 13 further comprising a removable lid for closing the top opening.

15. The burial container of claim 14 wherein the container body and lid are fashioned of steel reinforced concrete.

16. The burial container of claim 14 further comprising a plurality of rust-resistant lifting eyes secured to the lid to permit lifting of the lid from the container body.

17. The burial container of claim 14 further comprising a peripheral lip on the lid for engagement of the top opening when the lid is placed on the container body.

18. The burial container of claim 14 further comprising an indentation in the lid for reduction of weight.

* * * * *